United States Patent
Martin et al.

(10) Patent No.: US 12,034,810 B2
(45) Date of Patent: *Jul. 9, 2024

(54) CEILING FAN FOR ESTABLISHING A SYSTEM FOR LOCAL CONTROL OF A SPACE

(71) Applicant: Hubbell Incorporated, Shelton, CT (US)

(72) Inventors: Robert Conrad Martin, Tolland, CT (US); Brett Daniel Pare, Hartford, CT (US); Michael Richter, Canton, CT (US)

(73) Assignee: Hubbell Incorporated, Shelton, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/337,842

(22) Filed: Jun. 20, 2023

(65) Prior Publication Data

US 2023/0336627 A1    Oct. 19, 2023

Related U.S. Application Data

(63) Continuation of application No. 16/896,912, filed on Jun. 9, 2020, now Pat. No. 11,757,996.
(Continued)

(51) Int. Cl.
*H04L 67/125* (2022.01)
*A61B 5/00* (2006.01)
(Continued)

(52) U.S. Cl.
CPC ......... *H04L 67/125* (2013.01); *A61B 5/0022* (2013.01); *A61B 5/165* (2013.01);
(Continued)

(58) Field of Classification Search
CPC ........ G16H 20/00; G16H 40/67; G16H 10/20; G16H 80/00; G06N 20/00; A61B 3/04;
(Continued)

(56) References Cited

U.S. PATENT DOCUMENTS

2008/0265799 A1   10/2008   Sibert
2013/0030589 A1   1/2013    Pessina et al.
(Continued)

FOREIGN PATENT DOCUMENTS

WO   2015/171729 A1   11/2015

OTHER PUBLICATIONS

International Search Report and Written Opinion dated Sep. 9, 2020, by the International Searching Authority in corresponding International Patent Application No. PCT/US2020/36813. (14 pages).

*Primary Examiner* — James J Yang
*Assistant Examiner* — Anthony D Afrifa-Kyei
(74) *Attorney, Agent, or Firm* — Robinson & Cole LLP

(57) ABSTRACT

A ceiling fan for a space is provided. The ceiling fan can include a first communication interface configured to provide communications between the ceiling fan and a plurality of peripheral devices over a local network. The ceiling fan can further include a second communication interface configured to provide communications between the ceiling fan and an external network. The ceiling fan can further include one or more control devices configured to provide one or more control signals to control operation of one or more of the peripheral devices.

17 Claims, 8 Drawing Sheets

Related U.S. Application Data

(60) Provisional application No. 62/860,898, filed on Jun. 13, 2019.

(51) Int. Cl.

| | | |
|---|---|---|
| *A61B 5/16* | (2006.01) | |
| *A61L 9/12* | (2006.01) | |
| *F04D 25/06* | (2006.01) | |
| *F04D 27/00* | (2006.01) | |
| *F21V 23/00* | (2015.01) | |
| *F21V 33/00* | (2006.01) | |
| *G08C 17/00* | (2006.01) | |
| *H04W 84/18* | (2009.01) | |

(52) U.S. Cl.
CPC .............. *A61B 5/4803* (2013.01); *A61L 9/12* (2013.01); *F04D 25/06* (2013.01); *F04D 27/00* (2013.01); *F21V 23/003* (2013.01); *F21V 33/0096* (2013.01); *G08C 17/00* (2013.01); *A61L 2209/111* (2013.01); *G08C 2201/31* (2013.01); *G08C 2201/34* (2013.01); *G08C 2201/93* (2013.01); *H04W 84/18* (2013.01)

(58) Field of Classification Search
CPC ....... A61B 5/002; A61B 5/0022; A61B 5/165; A61B 5/4803; A61B 5/6889; A61B 2503/12; A61B 2505/07; A61B 2562/0204; A61B 2562/0247; G08C 17/00; G08C 2201/31; G08C 2201/34; A61L 9/12; A61L 2209/111; F04D 19/005; F04D 25/06; F04D 25/088; F04D 27/00; F04D 29/005; F21V 23/003; H04L 67/125

See application file for complete search history.

(56) References Cited

U.S. PATENT DOCUMENTS

| | | |
|---|---|---|
| 2014/0163751 A1 | 6/2014 | Davis et al. |
| 2014/0334653 A1* | 11/2014 | Luna ..................... H05B 47/12 |
| | | 600/27 |
| 2015/0086363 A1 | 3/2015 | Graziano et al. |
| 2015/0110625 A1 | 4/2015 | de Siqueira Indio da Costa et al. |
| 2015/0369503 A1* | 12/2015 | Flaherty ................. G06F 30/13 |
| | | 700/277 |
| 2016/0047391 A1 | 2/2016 | McPherson et al. |
| 2016/0259308 A1* | 9/2016 | Fadell .................... G05B 15/02 |
| 2016/0363920 A1 | 12/2016 | Chen et al. |
| 2019/0186496 A1 | 6/2019 | Monteith et al. |
| 2019/0335564 A1* | 10/2019 | Teshome ............... H04L 67/125 |
| 2019/0360649 A1* | 11/2019 | Puffer ................. F21V 23/0442 |

* cited by examiner

CEILING FAN FOR ESTABLISHING A SYSTEM FOR LOCAL CONTROL OF A SPACE

CROSS-REFERENCE TO RELATED APPLICATIONS

This application is a continuation of U.S. patent application Ser. No. 16/896,912, filed Jun. 9, 2020, which claims benefit of U.S. Provisional Patent Application No. 62/860,898, filed Jun. 13, 2019, the entire contents of which are incorporated by reference.

FIELD

The present disclosure relates generally to ceiling fans and, more particularly, to ceiling fans for local control of peripheral devices within a space.

BACKGROUND

Fans (e.g., ceiling fans) can be used to circulate air within a space. With the advance of Internet of Things (IoT) technology, in-home devices are configured to communicate over one or more communication links. For instance, devices can send and/or receive information using communication technologies, such as Bluetooth low energy, Bluetooth mesh networking, nearfield communication, Wi-Fi, ZigBee, Ethernet, etc.

BRIEF DESCRIPTION

Aspects and advantages of embodiments of the present disclosure will be set forth in part in the following description, or may be learned from the description, or may be learned through practice of the embodiments.

In one aspect, a ceiling fan for a space is provided. The ceiling fan can include a first communication interface configured to provide communications between the ceiling fan and a plurality of peripheral devices over a local network. The ceiling fan can further include a second communication interface configured to provide communications between the ceiling fan and an external network. The ceiling fan can further include one or more control devices configured to provide one or more control signals to control operation of one or more of the peripheral devices.

These and other features, aspects and advantages of the present disclosure will become better understood with reference to the following description and appended claims. The accompanying drawings that are incorporated in, and constitute a part of, this specification, illustrate embodiments of the present disclosure and, together with the description, serve to explain the principles of the disclosure.

BRIEF DESCRIPTION OF THE DRAWINGS

Detailed discussion of embodiments directed to one of ordinary skill in the art are set forth in the specification, which makes reference to the appended figures, in which.

DETAILED DESCRIPTION

Figure 1:
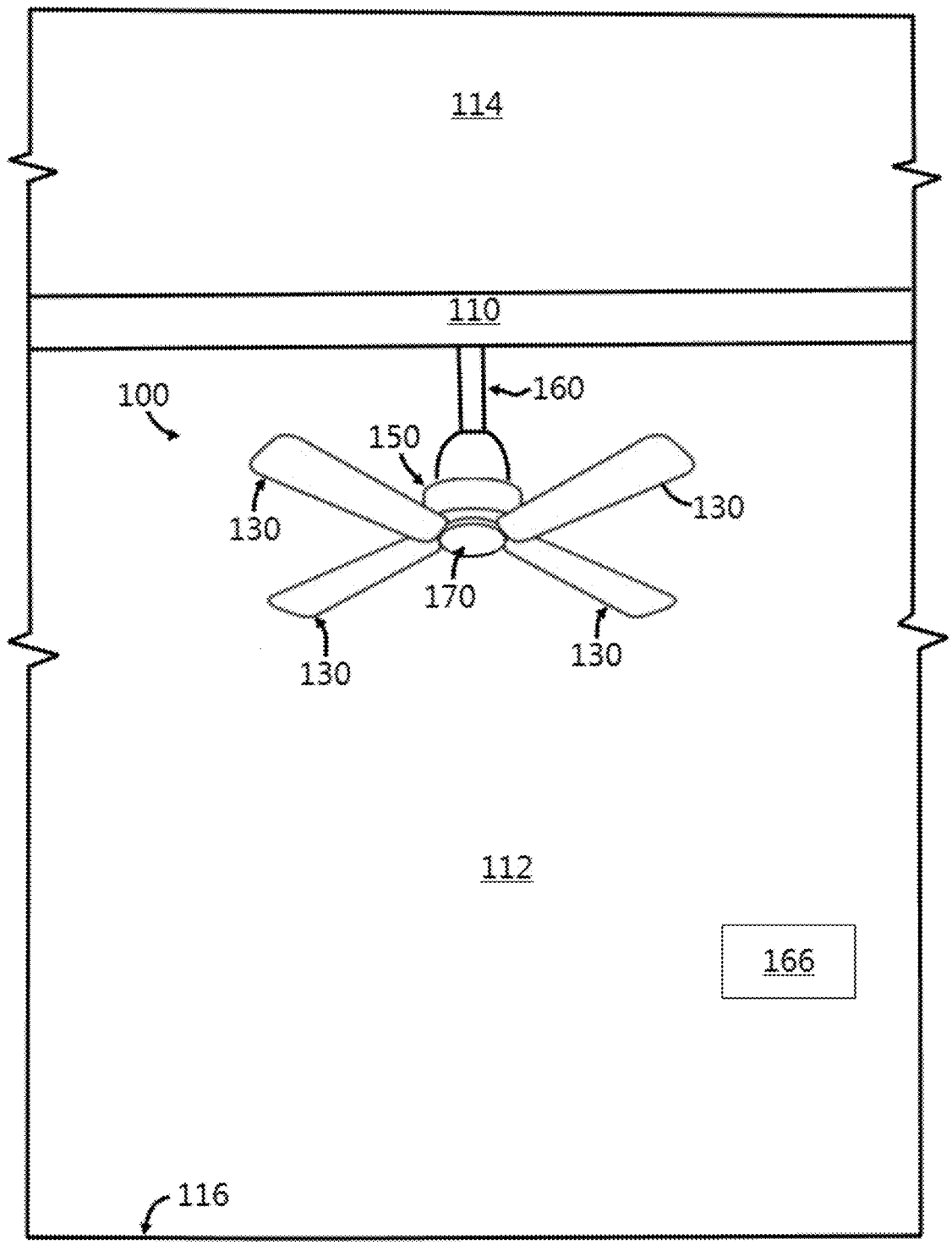
FIG. 1 provides a perspective view of a ceiling fan suspended from a ceiling according to exemplary embodiments of the present disclosure.

Reference is now made in detail to embodiments, one or more examples of which are illustrated in the drawings. Each example is provided by way of explanation of the exemplary embodiments and not limitation of the present disclosure. In fact, it will be apparent to those skilled in the art that various modifications and variations can be made to the embodiments without departing from the scope or spirit of the present disclosure. For instance, features illustrated or described as part of one exemplary embodiment can be used with another embodiment to yield a still further embodiment. Thus, it is intended that aspects of the present disclosure cover such modifications and variations.

Example aspects of the present disclosure are directed to a ceiling fan for a space, e.g., an indoor commercial or residential space or an outdoor space. The ceiling fan can include a first communication interface configured to provide communications between the fan and a plurality of peripheral devices located within the space over a local network. The ceiling fan can further include a second communication interface configured to provide communications between the fan and an external network. As will be discussed below in more detail, the ceiling fan can include one or more control devices configured to provide one or more control signals to control operation of one or more of the plurality of peripheral devices.

In some implementations, one or more of the plurality of peripheral devices within the space can be an air freshener dispenser. In such implementations, the one or more control devices of the fan can provide one or more control signals over the local network to control operation of the one or more air freshener dispensers. In particular, the one or more control signals can be associated with activating the one or more air freshener dispensers to dispense air freshener. In this manner, the scent of the space can be controlled via the one or more air freshener dispensers.

In some implementations, one or more of the plurality of peripheral devices can be a light source configured to illuminate the space. In particular, the one or more light sources can be separate from the fan. In such implementations, the one or more control devices of the fan can provide one or more control signals over the local network to control operation of the one or more light sources. For example, in some implementations, the one or more light sources can be dimmable light sources. In this manner, the one or more control signals can be associated with adjusting the intensity (e.g., brightness) of the light output of the one or more light sources. For instance, the one or more control signals can be associated with increasing the intensity of the light output. Conversely, the one or more control signals can be associated with decreasing the intensity of the light output.

In some implementations, the one or more control signals can be associated with adjusting a color and/or color temperature of the light output of the one or more light sources. For instance, the one or more control signals can be associated with adjusting the color of the light output from a first color to a second color that is different than the first color. It should be appreciated, however, that the one or more control devices of the fan can be configured to provide one or more control signals associated with adjusting one or more characteristic of the light output of the one or more light sources.

In some implementations, one or more of the plurality of peripheral devices located within the space can be an audio output device (e.g., a speaker). In such implementations, the one or more control devices of the fan can provide one or more control signals over the local network to control operation of the one or more audio output devices. In particular, the one or more control signals can be associated with broadcasting audio data (e.g., music) via the one or more audio output devices. In some implementations, the audio data can be associated with a streaming service (e.g., Spotify, iTunes, etc.). As will be discussed below in more detail, the one or more control devices can be configured to control operation of one or more of the peripheral devices according to a mood profile that corresponds to the mood of a user within the space.

In some implementations, a user can interact with a user interface implemented on, for instance, one or more computing devices (e.g., smartphone, tablet, etc.) to provide data indicative of the user's mood. The graphical user interface can, in some implementations, present a list of a plurality of predefined mood profiles for the space. Each of the plurality of mood profiles can include configuration data for at least one of the fan and the plurality of peripheral devices. The configuration data can be different for each of the plurality of mood profiles. In this manner, the each of the plurality of mood profiles can correspond to a different mood.

In some implementations, the user can select a mood profile from the list of the plurality of predefined mood profiles that corresponds to the mood of the user. For instance, the user can interact with an interface element to provide data indicative of a user request for a selected mood profile from the plurality of predefined mood profiles. In response to selecting the mood profile for the space via the graphical user interface, at least one of the fan and the plurality of peripheral devices can be configured according to the configuration data associated with the selected mood profile. In this manner, the atmosphere of the space can be configured according to the selected mood profile to correspond to the mood of the user within the space.

In some implementation, the graphical user interface can present a plurality of images. Each of the plurality of images can be associated with a corresponding mood profile of the plurality of mood profiles included in the list. For instance, the plurality of images can include a first image associated with a first mood profile (e.g., Mood Profile A) of the plurality of mood profiles included in the list. Furthermore, the plurality of images can include a second image associated with a second mood profile (e.g., Mood Profile B) of the plurality of mood profiles included in the list. The second image can be different than the first image. For instance, the first image can, in some implementations, be a smiley face emoji. Conversely, the second image can, in some implementations, be a crying face emoji. In this manner, the plurality of mood profiles can be distinguished from one another based, at in part on, the images.

In some implementations, the one or more control devices of the fan can be configured to determine a mood profile for the space based, at least in part, on data obtained from one or more sensors located within the space. The one or more sensors can, in some implementations, be included as part of the fan or one or more of the plurality of peripheral devices. Alternatively, the one or more sensors can, in some implementations, be separate from the peripheral devices. As will be discussed below in more detail, the one or more sensors can include any suitable type of sensors configured to obtain data indicative of a mood of a user within the space.

In some implementations, one or more of the sensors located within the space can be an audio input device (e.g., a microphone). In this manner, the one or more audio input devices can detect audio data indicative of audible noise associated with one or more verbal cues (e.g., sighing, laughing, crying, etc.) indicative of the user's mood. In such implementations, the one or more control devices of the fan can be configured to process audio data (e.g., either locally or remotely using a server or other remote device) indicative of the audible noise to determine a mood profile for the space based, at least in part, on the audio data. For instance, in some implementations the one or more control devices of the fan can be configured to select a mood profile from a plurality of predefined mood profiles for the space based, at least in part, on the audio data indicative of audible noise associated with one or more verbal cues indicative of the user's mood.

As an example, the one or more control devices of the fan can be configured to select a predefined mood profile corresponding to a happy mood in response to the one or more control devices determining the audio data indicative of audible noise detected by the one or more sensors includes one or more verbal cues (e.g., laughter) indicative of the user being in a happy mood. As another example, the one or more control devices of the fan can be configured to select a predefined mood profile corresponding to a sad mood in response to the one or more control devices determining the audio data indicative of audible noise detected by the one or more sensors includes one or more verbal cues (e.g., crying) indicative of the user being in a sad mood.

In some implementations, the one or more control devices of the fan can be configured to mute the one or more microphones when the user present within the space is on a call with another user via a mobile computing device (e.g., smartphone). In this manner, the one or more microphones cannot detect audible noises while the user is on the call. As such, the privacy of the call occurring within the space can be maintained.

In some implementations, one or more of the sensors can be configured to obtain data indicative of a location of the user within the space. For instance, one or more sensors can be a pressure sensor located at different locations within the space. In this manner, the one or more control devices of the fan can obtain data indicative of the location of the user within the space from the one or more pressure sensors. Furthermore, the one or more control devices of the fan can be configured to determine a mood profile for the space based, at least in part, on data obtained from the one or more pressure sensors and indicative of a location of the user within the space.

In some implementations, one or more of the sensors can be configured to detect ambient light levels within the space. In this manner, the one or more control devices of the fan can obtain data indicative of ambient light levels within the space from the one or more sensors. Furthermore, the one or more control devices of the fan can be configured to determine a mood profile for the space based, at least in part, on the data indicative of ambient light levels within the space. For instance, when data indicative of ambient light levels within the space indicates the ambient light levels are below a predetermined threshold, the one or more control devices of the fan can be configured to select a mood profile from a plurality of predefined mood profiles for the space that corresponds to a sad mood.

In some implementations, the one or more control devices of the fan can be configured to determine the mood profile for the space based, at least in part, on weather data associated with the space. For example, the one or more control devices of the fan can be configured to determine the mood profile for the space corresponds to a sad mood when the weather data indicates it is raining. As another example, the one or more control devices of the fan can be configured to determine the mood profile for the space corresponds to a happy mood when the weather data indicates it is sunny.

In some implementations, the one or more control devices of the fan can be configured to determine the mood profile for the space based, at least in part, on calendar data. For instance, the one or more control devices can be configured to access a calendar (e.g., Outlook) stored on a mobile computing device associated with the user present within the space. In this manner, the one or control devices of the fan can be configured to determine the mood profile for the space based, at least in part, on one or more events (e.g., birthday, graduation, etc.) included on the calendar. The one or more control devices of the fan can be configured to determine the mood profile based, at least in part, on data indicative of the current day and time.

In response to determining the mood profile for the space, the one or more control devices can be configured to provide one or more control signals over the local network to control operation of one or more of the peripheral devices according to the determined mood profile for the space. In this manner, the one or more control devices of the fan can configure the one or more peripheral devices within the space according to the mood of the user within the space.

The ceiling fan of the present disclosure can provide numerous technical benefits. For instance, the two separate communication interfaces can allow the ceiling fan to bridge communications between the external network and the local network. Furthermore, the one or control devices of the ceiling fan can be configured to determine a mood profile for the space that corresponds to the mood of a user within the space. Furthermore, the one or more control devices of the fan can control operation of one or more peripheral devices within the space according to the mood profile. In this manner, the ceiling fan can be configured to adjust the atmosphere of the space to accommodate the present mood of the user within the space.

As used herein, the term "mood profile" refers to configuration data for the ceiling fan within a space, one or more peripheral devices within the space, or both. In addition, the terms "first" and "second" may be used interchangeably to distinguish one component from another and are not intended to signify location or importance of the individual components.

Figure 2:
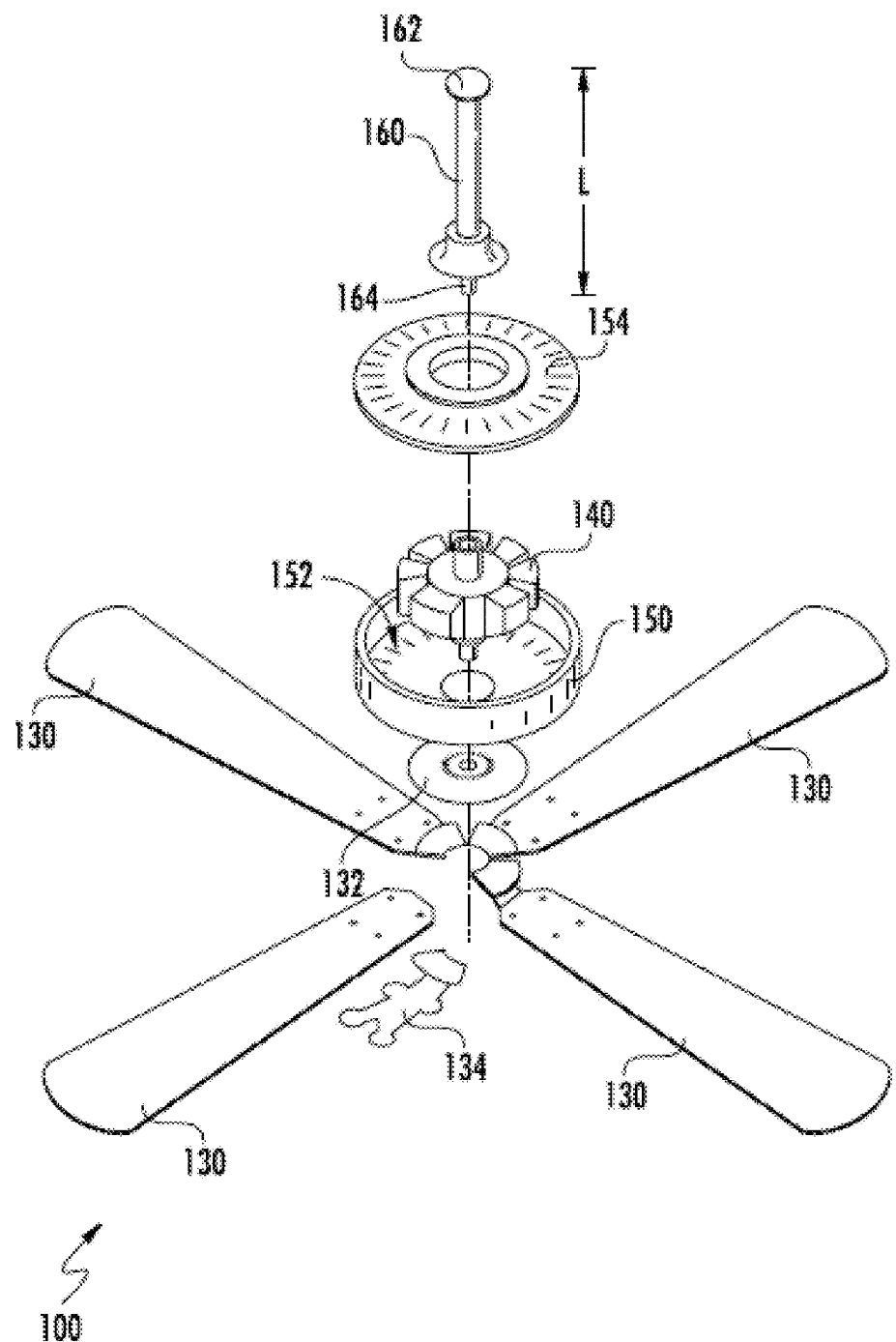
FIG. 2 provides an exploded view of a ceiling fan according to exemplary embodiments of the present disclosure.
Figure 3:
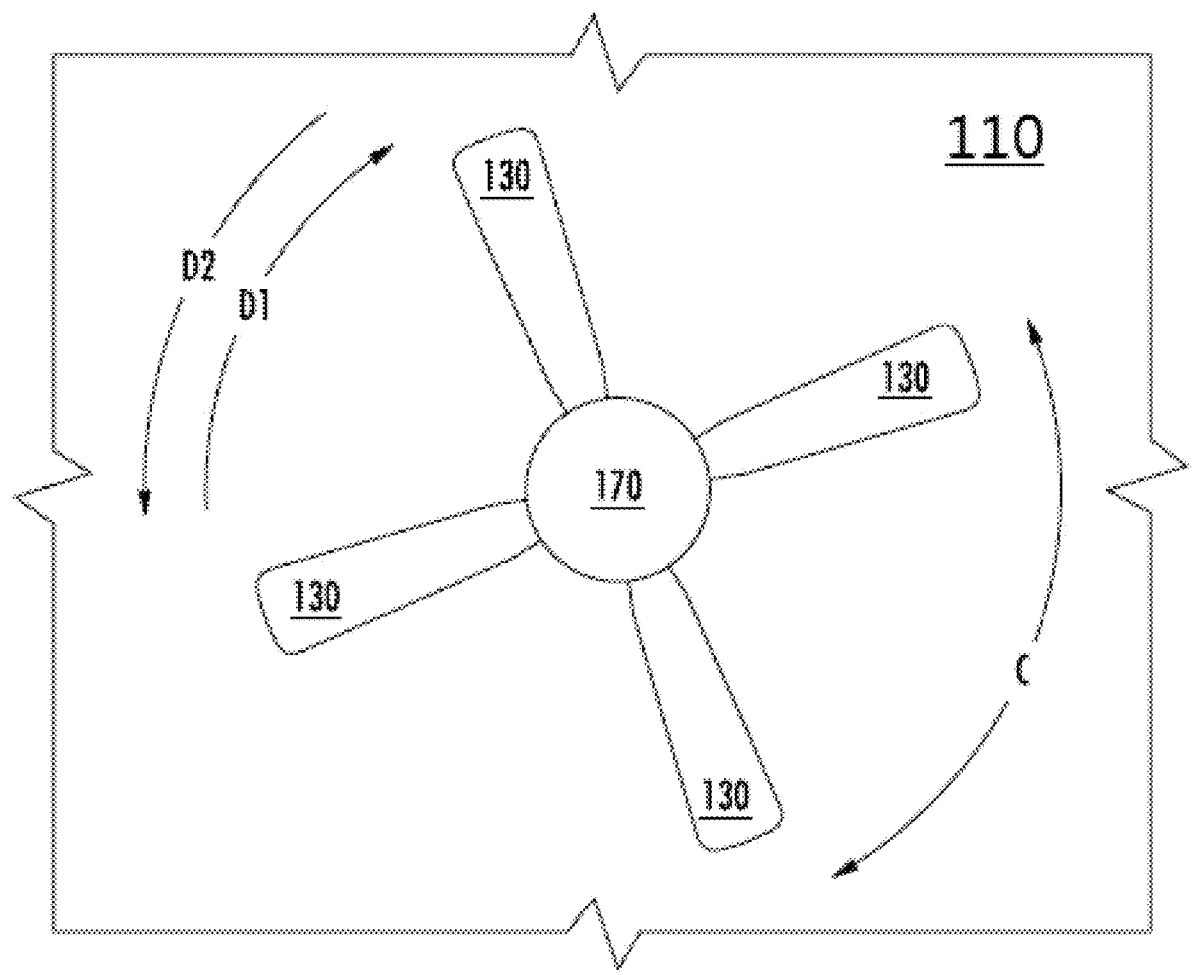
FIG. 3 provides a bottom-up view of a ceiling fan according to exemplary embodiments of the present disclosure.

Referring now to the figures, FIGS. 1 through 3 depict a ceiling fan 100 according to example embodiments of the present disclosure. The fan 100 can be removably mounted to a ceiling 110 separating a first space 112 (e.g., positioned beneath the ceiling 110) from a second space 114 (e.g., positioned above the ceiling 110). In some implementations, the fan 100 can include a plurality of fan blades 130. As shown, each the plurality of fan blades 130 can be coupled to a blade hub 132. More specifically, each of the fan blades 130 can be coupled to the blade hub 132 via a blade arm 134. It should be appreciated that the blade arm 134 can be coupled to the blade hub 132 and a corresponding fan blade 130 via any suitable type of fastener (e.g., screw, bolt, etc.). As shown, the fan blades 130 can be coupled to the blade hub 132 via the blade arm 134 such that the fan blades 130 are spaced apart from one another along a circumferential direction C.

In some implementations, the fan 100 can include a motor 140. The motor 140 can be configured to receive an input power from a power source, such as an alternating current (AC) power source or a direct current (DC) power source. Furthermore, the motor 140 can be operatively coupled to the fan blades 130 via the blade hub 132. In this manner, the motor 140 can convert the input power into mechanical energy needed to drive rotation of the fan blades 130 along the circumferential direction C. In some implementations, the motor 140 can be configured to drive rotation of the fan blades 130 in a first direction $D_1$ or a second direction $D_2$ that is different than the first direction $D_1$. For instance, the fan blades 130 can move air in the first space 112 towards the ceiling 110 when rotated in the first direction $D_1$. Conversely, the fan blades 130 can move air away from the ceiling 110 when rotated in the second direction $D_2$. More specifically, the fan blades 130 can move air towards a floor 116 defining the first space 112.

In some implementations, the fan 100 can include a fan motor housing 150 configured to accommodate the motor 140. More specifically, the motor 140 can be positioned within a cavity 152 defined by the fan motor housing 150. In addition, the fan 100 can include a cover 154 that can be coupled to the fan motor housing 150. In particular, the cover 154 can be coupled to the fan motor housing 150 such that the motor 140 positioned within the cavity 152 can be hidden from view.

As shown, the fan 100 can be suspended from the ceiling 110 via a downrod 160 having a first end 162 and a second end 164. It should be appreciated that the first end 162 and the second end 164 can be spaced apart from one another along a length L of the downrod 160. In example embodiments, the first end 162 of the downrod 160 can be coupled to a support (e.g., mounting bracket) positioned within the ceiling 110 or the second space 114. In addition, the fan motor housing 150 can be coupled to the second end 164 of the downrod 160.

In some implementations, the fan 100 can include a light source 170 operable to illuminate the first space 112. For instance, the light source 170 can be included within a lighting fixture (not shown) that can be removably coupled to the fan motor housing 150 via any suitable mechanical fastener (e.g., screws). It should be appreciated that the light source 170 can include any suitable type of light source configured to illuminate the first space 112. For instance, in some implementations, the light source 170 can include an array of light emitting diodes (LEDs).

In some implementations, operation of the fan 100 can be controlled by a control system 166. More specifically, the control system 166 can include a wall-switch that can be manipulated to selectively couple the motor 140 to a power supply. In this way, the control system 166 can selectively activate (e.g., turn on) or deactivate (e.g., turn off) the motor 140 to control rotation of the fan blades 130. In some implementations, the control system 166 can control operation of other devices. For instance, the control system 166 can be configured to adjust a position of window blinds (not shown) in the first space 112. More specifically, the control system 166 can adjust a position of the window blinds to or towards a fully open position or a fully closed position. In this way, an amount of natural light entering the first space 112 through one or more windows can be controlled.

Figure 4:
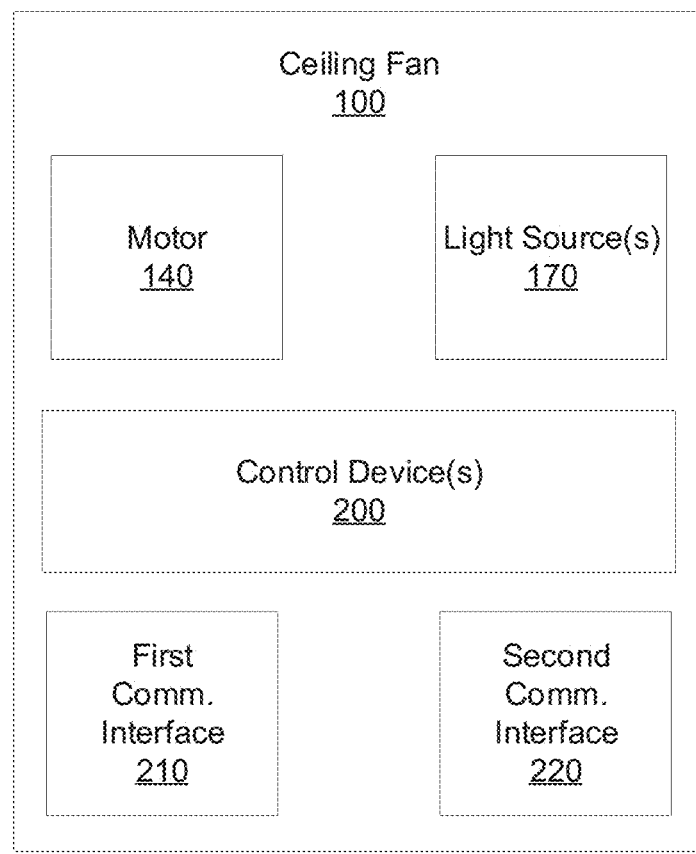
FIG. 4 provides a block diagram of components of a ceiling fan according to exemplary embodiments of the present disclosure.

Referring now to FIG. 4, the fan 100 can include one or more control devices 200. The fan can further include a first communication interface 210 and a second communication interface 220. The first communication interface 210 can be configured to provide communications between the fan 100 and one or more devices over a first network. For instance, in some implementations, the first network can be a Bluetooth network. In this manner, the fan 100 can communicate with one or more Bluetooth-enabled devices over the Bluetooth network. In some implementations, the first network can be a WiFi network. In this manner, the fan 100 can communicate with one or more Wifi-enabled devices over the WiFi network. In some implementations, the first network can be a LoRa network. In this manner, the fan 100 can communicate with one or more LoRa-enabled devices over the LoRa network. It should be appreciated, however, that the first network can include any suitable type of local network implementing any suitable type of protocol (e.g., Bluetooth, Wifi, Lora, etc.).

In some implementations, the second communication interface 220 can be configured to provide communications between the fan 100 and one or more devices over a second network that is different than the first network. For example, the second network can be a WiFi network. In this manner, the fan 100 can communicate with one or more WiFi-enabled devices over the WiFi network. As another example, the second network can be a cellular network. In this manner, the fan 100 can communicate with one or more cellular devices (e.g., smartphones, tablets, etc.) over the cellular network.

Figure 5:
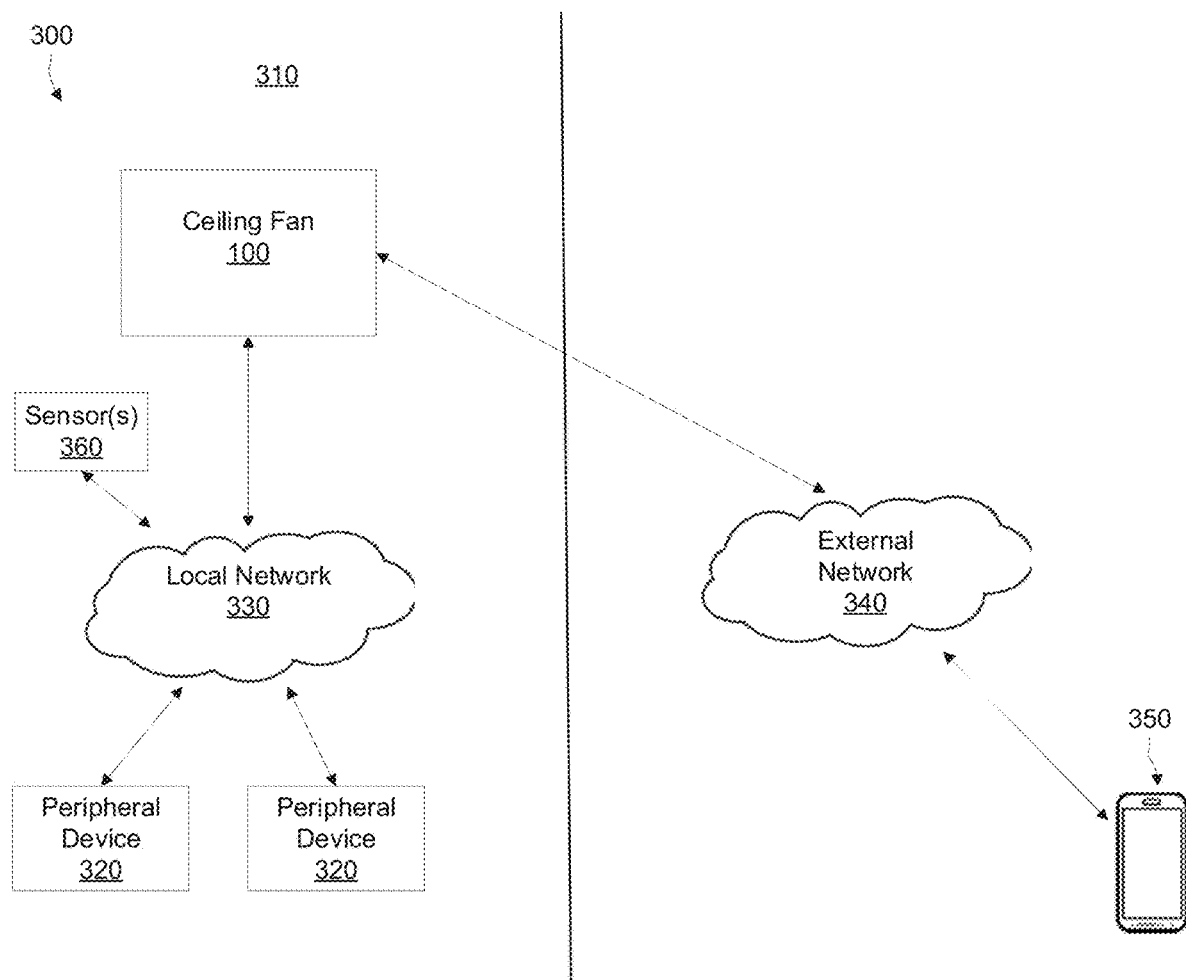
FIG. 5 provides a block diagram of components of a system according to exemplary embodiments of the present disclosure.

Referring now to FIG. 5, a system 300 for controlling conditions (e.g., scent, lighting, music, temperature, etc.) within a space 310 is provided according to example embodiments of the present disclosure. In some implementations, the space 310 can be a room of a residential home or apartment. For example, the space 310 can correspond to a bedroom or bathroom of the home or apartment. It should be appreciated, however, that the space 310 can correspond to any suitable room of the home or apartment. For instance, in some implementations, the space 310 can correspond to the den or living room of the home or apartment.

As shown, the system 300 can include the fan 100 and a plurality of peripheral devices 320. Furthermore, although the system 300 of FIG. 5 only includes two peripheral devices 320, it should be appreciated that the system 300 can include more or fewer peripheral devices 320. As will be discussed below, the one or more control devices 200 of the fan 100 can provide one or more control signals to control operation of one or more of the peripheral devices 320.

In some implementations, the first communication interface 210 (FIG. 4) of the fan 100 can be configured to provide communications between the fan 100 and the plurality of peripheral devices 320 over a local network 330 (e.g., first network). In this manner, the one or more control devices 200 (FIG. 4) of the fan 100 can provide one or more control signals over the local network 330 to control operation of one or more of the peripheral devices 320.

In some implementations, one or more of the plurality of peripheral devices 320 can be an air freshener dispenser. In such implementations, the one or more control devices 200 of the fan 100 can provide one or more control signals over the local network 330 to control operation of the one or more air freshener dispensers. In particular, the one or more control signals can be associated with activating the one or more air freshener dispensers to dispense air freshener. In this manner, the scent of the space 310 can be controlled via the one or more air freshener dispensers.

In some implementations, one or more of the plurality of peripheral devices 320 can be a light source that is separate from the fan 100. The one or more light sources can be configured to illuminate the space 310. In such implementations, the one or more control devices 200 of the fan 100 can provide one or more control signals over the local network 330 to control operation of the one or more light sources. For example, the one or more light sources can be dimmable light sources. In this manner, the one or more control signals can be associated with adjusting the intensity (e.g., brightness) of the light output of the one or more light sources. For instance, the one or more control signals can be associated with increasing the intensity of the light output. Conversely, the one or more control signals can be associated with decreasing the intensity of the light output.

In some implementations, the one or more control signals can be associated with adjusting a color and/or color temperature of the light output. For instance, the one or more control signals can be associated with adjusting the color of the light output from a first color to a second color that is different than the first color. It should be appreciated, however, that the one or more control devices 200 of the fan 100 can be configured to provide one or more control signals associated with controlling one or more characteristics of the light output of the one or more light sources.

In some implementations, one or more of the plurality of peripheral devices 320 located within the space can be an audio output device (e.g., speaker). In such implementations, the one or more control devices 200 of the fan 100 can provide one or more control signals over the local network to control operation of the one or more audio output devices. In particular, the one or more control signals can be associated with outputting audio data (e.g., music) through the one or more audio output devices. For example, in some implementations, the audio data can include a song or list of songs to be played through the one or more audio output devices.

In some implementations, one or more of peripheral devices 320 can be a thermostat of a heating ventilation and air-conditioning (HVAC) system used to cool or heat the space 310. In such implementations, the one or more control devices 200 of the fan 100 can provide one or more control signals over the local network 330 to the thermostat to control operation of the HVAC system. For instance, the one or more control signals provided to the thermostat can be associated with activating the HVAC system to heat or cool the space 310. Alternatively, the one or more control signals provided to the thermostat can be associated with deactivating the HVAC system to cease heating or cooling of the space 310 via the HVAC system.

In some implementations, one or more of the peripheral devices 320 can be a humidifier. In such implementations, the one or more control devices 200 of the fan 100 can provide one or more control signals to control operation of the humidifier. For instance, the one or more control signals can be associated with activating the humidifier to increase the humidity of air within the space 310. Conversely, the one or more control signals can be associated with deactivating the humidifier when the humidity of the air within the space 310 corresponds to a predetermined setpoint.

In some implementations, one or more of the peripheral devices 320 can be a dehumidifier. In such implementations, the one or more control devices 200 of the fan 100 can provide one or more control signals to control operation of the dehumidifier. For instance, the one or more control signals can be associated with activating the dehumidifier to decrease the humidity of air within the space 310. Conversely, the one or more control signals can be associated with deactivating the humidifier when the humidity of the air within the space 310 corresponds to a predetermined setpoint.

In some implementations, the second communication interface 220 (FIG. 4) of the fan 100 can be configured to provide communications between the fan 100 and an external network 340 (e.g., second network) that is separate from the local network 330. In this manner, the fan 100 can communicate with one or more mobile computing devices 350, such as a mobile telephone, tablet, laptop, or other similar wireless-enabled devices, over the external network 340. As will be discussed below in more detail, the fan 100 can be configured to control conditions within the space 310 based, at least in part, on data indicative of the mood of a user within the space 310.

Figure 6:
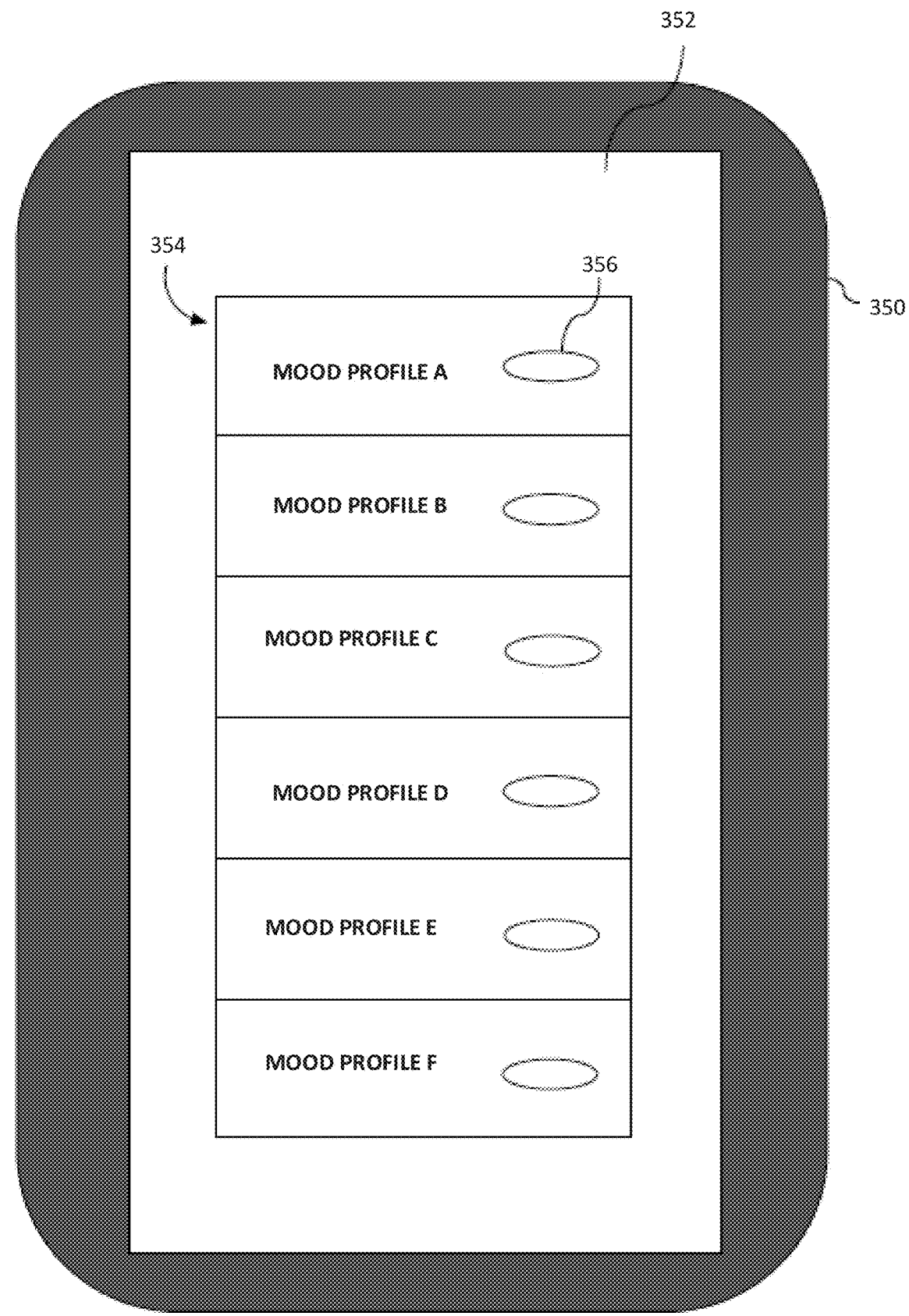
FIG. 6 provides an exemplary graphical user interface according to exemplary embodiments of the present disclosure.

Referring now to FIG. 6, a user can interact with a graphical user interface 352 implemented on, for instance, the one or more mobile computing devices 350 to provide data indicative of the user's mood. As shown, the graphical user interface 352 can present a list 354 of a plurality of predefined mood profiles for the space 310. Each of the plurality of mood profiles can include configuration data for at least one of the fan 100 and the plurality of peripheral devices 320. Furthermore, the configuration data can be different for each of the plurality of mood profiles such that each of the plurality of mood profiles corresponds to a different mood. The user can select a mood profile from the list 354 of the plurality of predefined mood profiles that corresponds to the mood of the user. For instance, the user can select the mood profile by interacting with an interface element, such as interface element 356. In this manner, at least one of the fan 100 and the plurality of peripheral devices 320 can be configured according to the configuration data associated with the selected mood profile to operate according to a mood profile that corresponds to the mood of the user.

In some implementation, the graphical user interface 352 can present a plurality of images. Each of the plurality of images can be associated with a corresponding mood profile of the plurality of mood profiles included in the list 354. For instance, the plurality of images can include a first image associated with a first mood profile (e.g., Mood Profile A) of the plurality of mood profiles included in the list 354. Furthermore, the plurality of images can include a second image associated with a second mood profile (e.g., Mood Profile B) of the plurality of mood profiles included in the list 354. The second image can be different than the first image. For instance, the first image can, in some implementations, be a smiley face emoji. Conversely, the second image can, in some implementations, be a crying face emoji. In this manner, the plurality of mood profiles can be distinguished from one another based, at in part on, the images.

In some implementations, the one or more control devices 200 of the fan 100 can be configured to determine a mood profile for the space 310 based, at least in part, on data obtained from a plurality of sensors 360 located within the space 310. In some implementations, one or more of the plurality of sensors 360 can be onboard the fan 100. Alternatively or additionally, one or more of the plurality of sensors 360 can be onboard one or more of the peripheral devices 320. In some implementations, one or more of the plurality of sensors 360 can be separate from the fan 100 and the plurality of peripheral devices 320.

In some implementations, one or more of the sensors 360 can be an audio input device (e.g., microphone). In this manner, the one or more microphones can detect audible noise associated with one or more verbal cues (e.g., sighing, laughing, crying, etc.) made by the user and indicative of the user's mood. In such implementations, the one or more control devices 200 of the fan 100 can be configured to process audio data indicative of the audible noise to determine the user's mood. Furthermore, the one or more control devices 200 of the fan 100 can be configured to select a mood profile from a plurality of predefined mood profiles for the space 310 based, at least in part, on the audio data indicative of the audible noise obtained from the one or more sensors 360. For example, the one or more control devices 200 of the fan 100 can be configured to select a predefined mood profile corresponding to a happy mood in response to the one or more control devices 200 determining the audio data indicative of audible noise detected by the one or more sensors 360 includes one or more verbal cues (e.g., laughter) indicative of the user being in a happy mood. As another example, the one or more control devices 200 of the fan can be configured to select a predefined mood profile corresponding to a sad mood in response to the one or more control devices 200 determining the audio data indicative of audible noise detected by the one or more sensors 360 includes one or more verbal cues (e.g., crying) indicative of the user being in a sad mood.

In some implementations, the one or more control devices 200 of the fan 100 can be configured to mute the one or more microphones when the user present within the space 310 is on a call with another user via a mobile computing device (e.g., smartphone). In this manner, the one or more microphones cannot detect audible noises while the user is on the call. As such, the privacy of the call occurring within the space 310 can be maintained.

In some implementations, the one or more sensors 360 can be configured to obtain data indicative of a location of the user within the space 310. For instance, the one or more sensors 360 can be pressure sensors located at different locations within the space 310. In this manner, the one or more control devices 200 of the fan 100 can obtain data indicative of the location of the user within the space 310 from the one or more sensors 360. Furthermore, the one or more control devices 200 of the fan 100 can be configured to determine the mood of the user within the space 310 based, at least in part, on data obtained from the one or more pressure sensors and indicative of a location of the user within the space 310.

In some implementations, the one or more sensors 360 can be configured to detect ambient light levels within the space 310. In this manner, the one or more control devices 200 of the fan 100 can obtain data indicative of ambient light levels within the space 310 from the one or more sensors 360. Furthermore, the one or more control devices 200 of the fan 100 can be configured to determine the mood of the user within the space 310 based, at least in part, on the data indicative of ambient light levels within the space 310. For instance, the one or more control devices 200 of the fan 100 can be configured to determine the user is in a sad mood when ambient light levels within the space 310 are below a predetermined threshold.

In some implementations, the one or more control devices 200 of the fan 100 can be configured to determine a mood profile for the space 310 based, at least in part, on the data obtained from the one or more sensors 360. Alternatively or additionally, the one or more control devices 200 of the fan 100 can be configured to determine the mood profile for the space 310 based, at least in part, on weather data associated with the space 310. For example, the one or more control devices 200 of the fan 100 can be configured to determine the mood profile for the space 310 corresponds to a sad mood when the weather data indicates it is raining. As another example, the one or more control devices 200 of the fan 100 can be configured to determine the mood profile for the space 310 corresponds to a happy mood when the weather data indicates it is sunny. In this manner, the weather data, the data obtained from the one or more sensors 360, or both can be used to determine the mood profile for the space 310.

In response to determining the mood profile for the space 310, the one or more control devices 200 can be configured to provide one or more control signals over the local network 330 to control operation of one or more of the peripheral devices 320 according to the determined mood profile for the space 310. For example, the one or more control signals can be associated with adjusting the color of the light output of one or more light sources within the space 310 according to the mood profile. Alternatively or additionally, the one or more control signals can be associated with activating one or more air freshener dispensers within the space 310 to dispense air freshener having a scent according to the mood profile and corresponding to the mood of the user with the space 310.

In some implementations, the one or more control signals can be associated with playing music via the one or more speakers according to the mood of the user within the space 310. For example, a first playlist or radio station can be played over the one or more speakers when the mood of the user within the space 310 corresponds to a happy mood. Alternatively, a second playlist or radio station that is different than the first playlist or radio station can be played over the one or more speakers when the mood of the user within the space 310 corresponds to a sad mood.

Figure 7:
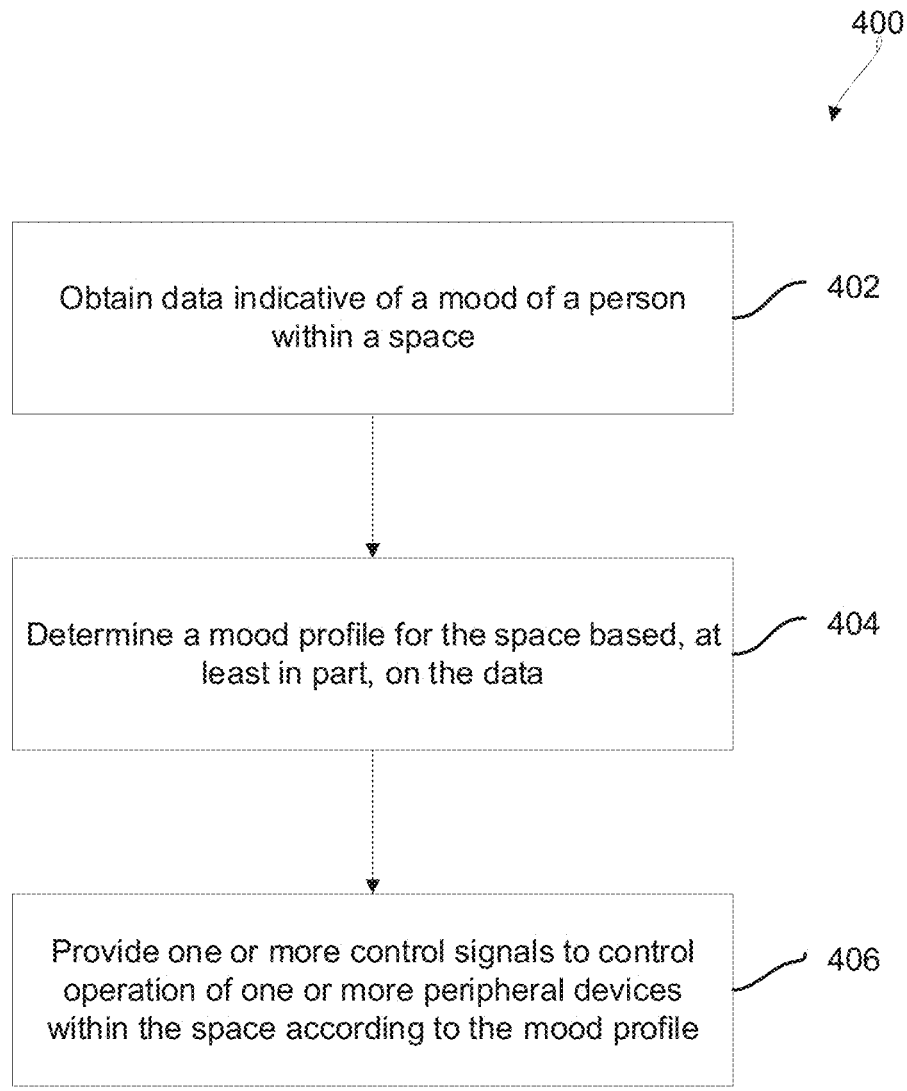
FIG. 7 provides flow diagram of a method for controlling conditions within a space using a system comprising a ceiling fan and a plurality of peripheral devices according to exemplary embodiments of the present disclosure.

Referring now to FIG. 7, a flow diagram of a method 400 for controlling conditions within a space using a system comprising a ceiling fan and a plurality of peripheral devices is provided according to example embodiments of the present disclosure. In general, the method 400 will be discussed herein with reference to the system 300 described above with reference to other figures, such as FIG. 5. However, it should be appreciated by those of ordinary skill in the art that the disclosed method 400 can generally be implemented with ceiling fans having any other suitable configuration. In addition, although FIG. 7 depicts steps performed in a particular order for purposes of illustration and discussion, the method discussed herein is not limited to any particular order or arrangement. One skilled in the art, using the disclosure provided herein, will appreciate that various steps of the method disclosed herein can be omitted, rearranged, combined, and/or adapted in various ways without deviating from the scope of the present disclosure.

At (402), the method 400 can include obtaining, by one or more control devices of a ceiling fan, data indicative of a mood of a user within the space. In some implementations, the data indicative of the mood of the user can be a user request for a selected mood profile from a plurality of mood profiles for the space. In particular, a user can interact with a user interface implemented on a mobile computing device to implement the user request for the selected mood profile for the space. It should be understood that the interaction can be a touch interaction, click interaction, or other interaction indicative of the user request for the selected mood profile for the space.

In some implementations, data indicative of the user's desired or programmed mood can be obtained via one or more sensors of the system. For example, the one or more sensors can be microphones configured to detect audible noise. In this manner, the one or more sensors can detect audible noise associated with one or more verbal cues (e.g., sighing, laughing, crying, etc.) indicative of the user's mood. In such implementations, the one or more control devices of the fan can be configured to process the audible noise associated with one or more verbal cues indicative of the user's mood. In this manner, the one or more control devices can determine the user's mood based, at least in part, on the audible noise detected by the one or more microphones.

At (404), the method 400 can include determining, by the one or more control devices, a mood profile for the space based, at least in part, on the data obtained at (402). In some implementations, the mood profile determined at (404) can correspond to a mood profile selected via the user interacting with a user interface implemented on a mobile computing device associated with the user. In some implementations, the data obtained at (402) can be indicative of the mood of more than one user within the space. For instance, the data obtained at (402) can include first data indicative of the mood of a first user within the space and second data indicative of the mood of a second user within the space. In such implementations, the one or more control devices can be configured to determine the mood profile for the space based, at least in part, on the first data and the second data. More specifically, the one or more control devices can be configured to determine a mood profile that accommodates the mood of the first user and the mood of the second user. For instance, the one or more control devices can be configured adjust first configuration data associated with a first mood profile corresponding to the mood of the first user and second configuration data associated with a second mood profile corresponding to the mood of the second user to generate configuration data for a third mood profile that represents a blend of the first mood profile and the second mood profile.

At (406), the method 400 can include providing, by the one or more control devices of the fan, one or more control signals to control operation of one or more of the peripheral devices based, at least in part, on mood profile determined at (404). In some implementations, the one or more control signals can be provided over a local network to control operation of the one or more peripheral devices according to the selected mood profile for the space. In this manner, the one or more peripheral devices can be controlled according to the data obtained at (402).

Figure 8:
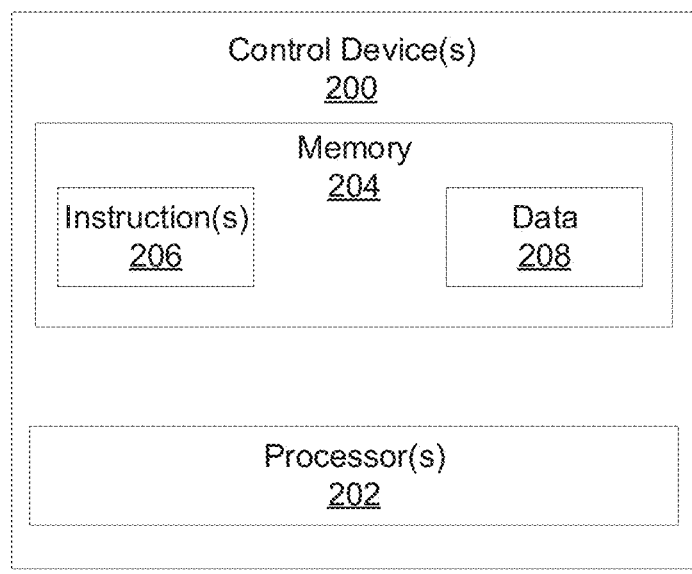
FIG. 8 provides a block diagram of components of a control device according to exemplary embodiments of the present disclosure.

FIG. 8 illustrates one embodiment of suitable components of the one or more control devices 200. As shown, the control device(s) 200 can include one or more processors 202 configured to perform a variety of computer-implemented functions. As used herein, the term "processor" refers not only to integrated circuits referred to in the art as being included in a computer, but also refers to a controller, microcontroller, a microcomputer, a programmable logic controller (PLC), an application specific integrated circuit (ASIC), a Field Programmable Gate Array (FPGA), and other programmable circuits.

In addition, the control device(s) 200 can include a memory device 204. Examples of the memory device 204 can include computer-readable media including, but not limited to, non-transitory computer-readable media, such as RAM, ROM, hard drives, flash drives, or other suitable memory devices. The memory device 204 can store information accessible by the processor(s) 202, including computer-readable instructions 206 that can be executed by the processor(s) 202. The computer-readable instructions 206 can be any set of instructions that, when executed by the processor(s) 202, cause the processor(s) 202 to perform operations. The computer-readable instructions 206 can be software written in any suitable programming language or can be implemented in hardware. In some example embodiments, the computer-readable instructions 206 can be executed by the control device(s) 200 to perform operations, such as providing one or more control signals to control operation of one or more peripheral devices of a system for a space. The memory device 204 can further store data 208 that can be accessed by the control device(s) 200. In example embodiments, the data 208 can include a plurality of predefined mood profiles for a space in which the fan and peripheral devices are located.

While the present subject matter has been described in detail with respect to specific example embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A ceiling fan for a space, the ceiling fan comprising:
a first communication interface configured to provide communications between the ceiling fan and a plurality of peripheral devices over a local network;
a second communication interface configured to provide communications between the ceiling fan and an external network; and
one or more control devices configured to provide one or more control signals, via the first communication interface, to control operation of one or more of the peripheral devices, based on data indicative of a mood profile for the space,
wherein the one or more control devices are configured to receive the data indicative of the mood profile for the space from a user to the ceiling fan via the second communication interface.

2. The ceiling fan of claim 1, wherein the data indicative of the mood profile for the space received from the user is based on audio data associated with one or more verbal cues indicative of the mood of the user.

3. The ceiling fan of claim 1, wherein:
the local network comprises a Bluetooth network; and
the external network comprises a Wifi network or a cellular network.

4. The ceiling fan of claim 1, wherein the data indicative of the mood profile for the space received from the user is based on weather data, calendar data, event data, ambient light data, or time of day data.

5. The ceiling fan of claim 1, further comprising:
one or more fan blades; and
a motor operatively coupled to the one or more fan blades, the motor configured to drive rotation of the one or more fan blades.

6. A method for controlling conditions within a space using a system comprising a ceiling fan and a plurality of peripheral devices,
wherein the ceiling fan comprises:
a first communication interface configured to provide communications between the ceiling fan and the plurality of peripheral devices over a local network;
a second communication interface configured to provide communications between the ceiling fan and an external network; and
one or more control devices,
the method comprising:
receiving, by the one or more control devices of the ceiling fan, data indicative of a mood profile for the space from a user to the ceiling fan via the second communication interface; and
providing, by the one or more control devices, via the first communication interface, one or more control signals to control operation of one or more of the peripheral devices of the system based on the data indicative of the mood profile for the space.

7. The method of claim 6, wherein one or more of the plurality of peripheral devices comprise at least one selected from an air freshener dispenser and a light source.

8. The method of claim 7, the one or more control signals are associated with controlling operation of the air freshener dispenser to dispense air freshener having a scent corresponding to the mood profile selected by the user.

9. The method of claim 7, wherein the one or more control signals are associated with adjusting one or more characteristics of a light output of the light source according to the mood profile selected by the user.

10. The method of claim 9, wherein the one or more characteristics of the light output include a color of the light output.

11. The method of claim 6, comprising obtaining, by the one or more control devices, data indicative of a mood of a user within the space from one or more sensors within the space.

12. The method of claim 11, wherein the one or more sensors comprise at least one selected from a microphone and a pressure sensor.

13. The method of claim 11, wherein the data indicative of the mood of the user comprises audio data indicative of the mood of the user.

14. The method of claim 13, comprising:
determining a second mood profile for the space by processing, by the one or more control devices, the audio data; and
providing, by the one of more control devices, one or more second control signal to control operation of at least one of the peripheral devices of the system according to the determined second mood profile.

15. A system for controlling conditions in a space, the system comprising:
a plurality of peripheral devices; and
a ceiling fan comprising:
a first communication interface configured to provide communication between the plurality of peripheral devices and the ceiling fan over a local network;

a second communication interface configured to provide communications between the ceiling fan and an external network; and one or more control devices configured to provide one or more control signals over the local network, via the first communication interface, to control operation of the plurality of peripheral devices, based on data indicative of a mood profile for the space, wherein the one or more control devices are configured to receive the data indicative of the mood profile for the space from a user to the ceiling fan via the second communication interface.

16. The system of claim 15, wherein the data indicative of the mood profile for the space received from the user is based on audio data associated with one or more verbal cues indicative of the mood of the user.

17. The system of claim 15, wherein the data indicative of the mood profile for the space received from the user is based on weather data, calendar data, event data, ambient light data, or time of day data.

\* \* \* \* \*